United States Patent [19]

Arena

[11] Patent Number: 4,496,780
[45] Date of Patent: Jan. 29, 1985

[54] HYDROCRACKING OF POLYOLS

[75] Inventor: Blaise J. Arena, Des Plaines, Ill.

[73] Assignee: UOP Inc., Des Plaines, Ill.

[21] Appl. No.: 507,198

[22] Filed: Jun. 22, 1983

[51] Int. Cl.$^3$ .................... C07C 29/132; C07C 31/20; C07C 31/22

[52] U.S. Cl. .................. 568/861; 502/327; 568/863

[58] Field of Search ............... 568/861, 863

[56] References Cited

U.S. PATENT DOCUMENTS

| | | | |
|---|---|---|---|
| 2,965,679 | 12/1960 | Conradin et al. | 568/861 |
| 3,030,429 | 4/1962 | Conradin et al. | 568/863 |
| 3,055,840 | 9/1962 | Koch | 568/863 |
| 3,396,199 | 8/1968 | Kasehagen | 568/863 |
| 3,459,814 | 8/1969 | Kovach et al. | 568/861 |
| 3,759,845 | 9/1973 | Rudoff et al. | 568/861 |
| 4,326,072 | 4/1982 | Kruse et al. | 568/863 |
| 4,366,332 | 12/1982 | Chao et al. | 568/863 |
| 4,404,411 | 9/1983 | Tanikella | 568/861 |

*Primary Examiner*—J. E. Evans
*Attorney, Agent, or Firm*—James R. Hoatson, Jr.; Raymond H. Nelson; William H. Page, II

[57] ABSTRACT

Polyols such as carbohydrates including glucose, fructose, sorbitol, etc. may be subjected to a hydrocracking process to obtain lower polyols such as glycerol, ethylene glycol, 1,2-propanediol. The catalyst system which is used to effect this reaction will comprise a noble metal of Group VIII of the Periodic Table composited on a solid support plus an alkaline earth metal oxide, an example of this catalyst system being ruthenium composited on a titanited alumina support plus barium oxide.

1 Claim, No Drawings 4,496,780

HYDROCRACKING OF POLYOLS

BACKGROUND OF THE INVENTION

Carbohydrates which contain a plurality of hydroxy substituents will be defined in the following specification and appended claims as polyols. The carbohydrates which may be classified as monosaccharides or polysaccharides are generally found in nature. Some of the carbohydrates possess desirable characteristics which enable them to be utilized for a wide variety of purposes in industry. For example, glucose or fructose are widely used as sweetening agents in confections, food stuffs, etc. Other carbohydrates or polyols such as sorbitol which is the polyol reduction product obtained from glucose may be used for the synthesis of resins, surface active agents, varnishes, in explosive manufacture, etc. While the carbohydrates such as monosaccharides which may contain from 4 to about 6 carbon atoms such as tetroses, pentoses, hexoses, etc. as well as polysaccharides such as starch, cellulose, etc. are widely found in nature and are therefore relatively inexpensive to obtain, lower polyols or diols are also useful in many industries.

As an example of lower polyols which are useful in industry, glycerol is a prime illustration. This compound may be used in alkyd resins, explosives, in pharmaceutical compounds, in perfumery, cosmetics, as a preservative or sweetening agent in foodstuffs, as a solvent, emulsifying agent, binder for cements and mixes, as an antifreeze agent, as a lubricant and softener, as a bacteriostat, humectant, etc. Glycerol may be prepared from the spent lye liqueur from the saponification of fats and oils in the soap industry, by precipitation of salt, albumin oils, and catalytic soaps of the higher fatty acids utilizing iron persulfate or aluminum sulfate in concentration with a subsequent steam distillation. Another method of preparing glycerol is by the chlorination and hydrolysis of propylene or allyl alcohol; or by the reaction of acrolein and hydrogen peroxide followed by reduction of the glyceraldehyde. Another polyol which finds a wide variety of uses is ethylene glycol which, like glycerol, may also be used as an antifreeze, as a coolant in motors, in the manufacture of explosives, as a dye solvent, in the manufacture of lacquers, resins, printing inks, etc. This compound has been prepared by heating ethylene chlorohydrin with a solution of an alkali carbonate or bicarbonate; by the oxidation of ethylene with air followed by hydration of the ethylene oxide which is formed or from the reaction of formaldehyde, water and carbon monoxide to form glycolic acid followed by hydrogenation to obtain the desired product.

It is readily apparent that the lower polyols such as those described are important articles of commerce, being widely used in a variety of chemical industries. However, processes for obtaining these polyols have been relatively complicated in nature and usually involve a number of steps in the process in order to obtain a desired product. As will hereinafter be shown in greater detail, it has now been discovered that lower polyols may be obtained by hydrocracking a higher polyol in the presence of certain catalytic compositions of matter which will permit the recovery of the desired products in a greater yield than has heretofore been provided.

BRIEF DESCRIPTION OF THE INVENTION

This invention relates to a process for the hydrocracking of carbohydrates. More specifically, the invention is concerned with a hydrocracking process involving carbohydrate-derived polyols utilizing certain catalytic compositions of matter to obtain a greater yield of the desired product than has heretofore been possible.

It is therefore an object of this invention to provide a process for the hydrocracking of polyols.

A further object of this invention is found in a catalyst system useful for obtaining greater yields of hydrocracked products obtained by the hydrocracking of carbohydrate-derived polyols.

In one aspect an embodiment of this invention resides in a process for the hydrocracking of a polyol which comprises treating said polyol at hydrocracking conditions in the presence of hydrogen and a catalyst system comprising a noble metal of Group VIII of the Periodic Table composited on a solid support and an alkaline earth metal oxide, and recovering the resultant hydrocracked products.

A specific embodiment of this invention resides in a process for the hydrocracking of a polyol which comprises treating sorbitol at a temperature in the range of from about 150° to about 250° C. and a pressure in the range of from about 500 to about 5000 pounds per square inch gauge (psig) in the presence of hydrogen and catalyst system comprising ruthenium composited on a titanited gamma-alumina support and barium oxide, and recovering the resultant products comprising glycerol, ethylene glycol and 1,2-propanediol.

Other objects and embodiments will be found in the following further detailed description of the present invention.

DETAILED DESCRIPTION OF THE INVENTION

As hereinbefore set forth, the present invention is concerned with a process for the hydrocracking of polyols by treating the polyols at hydrocracking conditions in the presence of hydrogen and a catalyst system of the type hereinafter set forth in greater detail. As was previously stated, it has now been discovered that by utilizing the catalyst system herein described, it is possible to obtain greater yields of lower polyols which are useful compounds in industry. The polyols which undergo hydrocracking according to the process of this invention comprise carbohydrates including both monosaccharides and polysaccharides. Some specific examples of these carbohydrates will include hexoses, pentoses, and tetroses such as glucose, mannose, galactose, talose, fructose, allose, iodose, gulose, xylose, lyxose, ribose, arabinose, threose, erythrose, etc., sorbitol, mannitol, etc., disaccharides such as maltose, cellobinose, sucrose, lactose, etc.; polysaccharides such as starch, cellulose, etc. It is to be understood that the aforementioned polyols are only representative of the class of compounds which may be hydrocracked according to this process and that the invention is not necessarily limited thereto.

The aforementioned polyols are subjected to hydrocracking by treatment with hydrogen at hydrocracking conditions which will include temperatures in the range of from about 150° up to about 250° C. or more and at pressures which range from about 500 up to about 5000 psig. The operating pressures at which the hydrocracking is effected will be afforded by the hydrogen per se, although it is also contemplated within the scope of this invention that, if so desired, the presence of hydrogen may account for only a partial pressure, the remainder of the desired pressure being afforded by the introduction or presence of a substantially inert gas such as nitrogen, helium, argon, etc. in the reaction vessel.

The catalyst system which is utilized to effect the hydrocracking of the polyol will comprise a noble metal of Group VIII of the Periodic Table composited on a support and an alkaline earth metal oxide. Examples of noble metals of Group VIII of the Periodic Table which may be utilized will include ruthenium, rhodium, osmium, iridium, platinum and palladium. The solid supports on which the noble metal of Group VIII of the Periodic Table may be composited will comprise, in the preferred embodiment of the invention, a metal oxide and preferably a metal oxide which possesses a relatively high surface area. Examples of these metal oxides will include aluminas such as gamma-alumina, theta-alumina, eta-alumina, silica, and mixtures of metal oxides such as silica-alumina. Again, in the preferred embodiment of the invention, the metal oxide which will act as a support for the noble metal will be pretreated, prior to impregnation with the noble metal, with a titanium-containing compound to prepare a titanited metal oxide. For example, an alumina such as gamma-alumina may be treated with titanium tetrachloride in a manner hereinafter set forth in greater detail to prepare a titanited alumina which may contain from about 1 to about 5% by weight of titanium. Following this, the noble metal may be composited on the titanited support by impregnating the titanited support with an aqueous or nonaqueous solution of a noble metal-containing compound for a period of time sufficient to impart a noble metal content of from about 1% to about 10% by weight of the finished composite. The cocatalyst which is present in the catalyst system utilized in the hydrocracking of polyols will comprise an alkaline earth metal oxide, specific examples of these compounds including beryllium oxide, magnesium oxide, calcium oxide, strontium oxide and barium oxide. In the preferred embodiment of the invention, the barium oxide may be present in the catalyst system in an amount within the range of from about 5% to about 50% by weight of the finished catalyst system.

The process of the present invention may be effected in any suitable manner and may comprise either a batch or continuous type operation. For example, when a batch type operation is employed, a quantity of the catalyst system and the polyol may be placed in an appropriate apparatus which is of the pressure-resistant type, examples of this type of apparatus include autoclaves of the mixing, stirring, rotating type. The autoclave is sealed and hydrogen is charged thereto until an initial operating pressure within the range hereinbefore set forth has been reached. Following this, the autoclave is then heated to the desired operating temperature and the hydrocracking reaction is allowed to proceed for a predetermined period of time which may range from about 0.5 up to about 10 hours or more in duration, the residence time of the reaction being dependent upon the particular operating parameters of temperature and pressure as well as feedstock which are employed. Upon completion of the desired residence time, heating is discontinued and, after the autoclave and contents thereof have returned to room temperature, excess pressure is discontinued and the autoclave is opened. The reaction mixture is recovered from the autoclave, separated from the catalyst system by conventional means such as filtration, decantation, ion exchange, etc. and the liquid is subjected to fractional distillation whereby the lower polyols, which include diols, are separated and recovered.

In addition to the batch type of operation, it is also contemplated that a continuous method of operation may also be employed to effect the desired hydrocracking of polyols. When a continuous type of operation is used, the feedstock comprising the high molecular weight polyols is continuously charged to a reaction vessel which is maintained at the proper operating conditions of temperature and pressure. After passage through the reactor for a predetermined period of time while being contacted with hydrogen, also continuously supplied to the reactor, the reactor effluent is withdrawn and subjected to conventional means of separation whereby any other reacted polyol is separated from the lower polyols and recycled back to the reactor to form a portion of the feedstock, the lower polyols also being separated into the various constituents and recovered.

Inasmuch as the catalyst system is solid in nature, it is possible to employ various types of continuous operations which may be employed comprising a fixed bed method in which the catalyst system is positioned as a fixed bed in the reactor and the polyol comes in contact with the catalyst bed in either an upward or downward flow. Another type of operation which may be employed comprises a moving bed operation in which the catalyst bed and the feedstock comprising the polyol are passed through the reactor either concurrently or countercurrently to each other. Alternatively, a slurry-type operation may be employed in which the catalyst system comprising the noble metal of Group VIII of the Periodic Table composited on a titanite solid support and the alkaline earth metal oxide are carried into the reactor as a slurry in the feedstock. In each type of operation, the reactor effluent which is continuously withdrawn from the reactor is treated in a manner similar to that hereinbefore set forth whereby catalyst is separated from the reaction mixture, the latter also being separated into desired products and unreacted starting material, the latter being recycled back to the reactor to form a portion of the feedstock which is charged thereto.

The following examples are given for purposes of illustrating the process of the present invention and the catalyst system which is employed to hydrocrack the polyols. However, it is to be understood that these examples are merely illustrative in nature and that the present process is not necessarily limited thereto.

EXAMPLE I

In this example, gamma-alumina spheres (250 g) were treated with a neat solution of titanium tetrachloride for 15 minutes at room temperature. Following this, the excess titanium tetrachloride was decanted off and the impregnated alumina was then heated at a temperature of 150° C. in a nitrogen atmosphere to boil off the remaining excess titanium tetrachloride. Thereafter, the impregnated alumina was calcined at a temperature of 500° C. for a period of 3 hours in an air atmosphere, the finished support being found to contain 1.97% by weight of titanium.

Thereafter, 0.8 g of ruthenium trichloride was dissolved in 50 ml of deionized water, the solution was added to 10 g of the titanited gamma-alumina prepared according to the above paragraph and mixed for a period of 0.5 hour. At the end of this time, the ruthenium trichloride solution was evaporated by utilizing a steam bath. The ruthenium trichloride impregnated support was then heated to a temperature of 400° C. in a flowing nitrogen atmosphere for a period of 3 hours followed by 3 hours at 400° C. in flowing hydrogen to activate the catalyst.

EXAMPLE II

In this example, 4.9 g of barium oxide was dissolved in 100 ml of deionized water and 20 g of titanited gamma-alumina prepared according to the method set forth in Example I above was added thereto. The mixture was allowed to stand for 16 hours following which the barium oxide solution was filtered and the treated titanited alumina support material was washed with water to remove excess barium. The support was then dried at a temperature of 105° C. and was found to contain 7.88% by weight of barium.

The catalyst system was then prepared by dissolving 1.56 g of ruthenium trichloride in 50 ml of deionized water and mixing the solution with 20 g of the barium treated titanited alumina for a period of 0.5 hours. Following this, the ruthenium trichloride solution was evaporated from the support using a steam bath and the impregnated material was then treated in a flowing nitrogen atmosphere at a temperature of 250° C. for a period of 3 hours followed by activation in flowing hydrogen for an additional period of 3 hours at the same temperature.

EXAMPLE III

To illustrate the efficacy of a catalyst system consisting of an alkaline earth metal oxide plus a ruthenium on a titanited alumina support as opposed to a catalyst system containing both the alkaline earth metal and the ruthenium composited on a single support, sorbitol was subjected to a hydrocracking process. The reaction was effected by placing 50 g of a 50% aqueous sorbitol solution in a sealed rotating bomb reactor which was then heated to a temperature of 180° C. for a period of 4 hours, hydrogen being pressed in until a pressure of 3200 psig had been reached, and maintained.

The results of these tests are set forth in Table 1 below in which catalyst "A" comprised 2.0 g of the catalyst of Example I plus 1.0 g of barium oxide, while catalyst "B" comprised 2.0 g of the material prepared according to Example II.

TABLE 1

| Catalyst | A | B |
| --- | --- | --- |
| Total Polyol Conversion | 57.6% | 23.6% |
| Yield of: | | |
| ethylene glycol | 3.1% | — |
| glycerol | 21.5% | 7.8% |
| 1,2-propanediol | 18.3% | — |

It is obvious from a comparison of the results obtained form the two runs as set forth in Table 1 above that a catalyst system comprising a noble metal of Group VIII of the Periodic Table such as ruthenium composited on a titanited alumina support plus a cocatalyst of an alkaline earth metal oxide such as barium oxide compared to a catalyst system in which both the alkaline earth metal and the noble metal of Group VIII of the Periodic Table are composited on a single support that the former catalyst system will result in a total polyol conversion twice as great as that obtained when using the latter plus a yield of lower polyols which are six times greater.

EXAMPLE IV

In a manner similar to that set forth in Example I above, one component of the catalyst system which is used in the present invention may be prepared by treating gamma-alumina spheres with a neat solution of titanium tetrachloride for a period of 15 minutes. After treatment with the titanium tetrachloride, the excess solution may be removed by decantation and the impregnated alumina may then be heated to a temperature of 150° C. in a flowing nitrogen atmosphere to remove the remaining excess titanium tetrachloride. Following this, the impregnated alumina may then be calcined at a temperature of about 500° C. for a period of three hours in an air atmosphere. The titanited alumina may then be further impregnated by preparing a solution of rhodium nitrate in deionized water and adding the titanited alumina thereto. After allowing the mixture to stand for a period of 0.5 hour, the excess rhodium nitrate solution may be evaporated by placing the mixture on a steam bath. After evaporation of the rhodium nitrate has been completed, the rhodium impregnated titanited alumina may then be heated to a temperature of about 300° C. in a flowing nitrogen atmosphere and activated by subjecting the catalyst to a hydrogen flow for an additional period of three hours at this temperature.

The thus prepared catalyst may be used as one component of a catalyst system in a hydrocracking process by placing 2 g of this catalyst and 1 g of calcium oxide in an autoclave along with 50 cc of mannitol. The autoclave may then be sealed and hydrogen pressed in until an initial operating pressure of 3000 psig has been reached. The autoclave may then be heated to a temperature of 180° C. and maintained thereat for a period of four hours. At the end of this time, heating may be discontinued and after the autoclave has returned to room temperature, the excess pressure may be discharged and the autoclave opened, following which the reaction product comprising a mixture of lower polyols such as ethylene glycol, glycerol and 1,2-propanediol being recovered therefrom.

EXAMPLE V

One component of the catalyst system may be prepared by treating gamma-alumina spheres with an aqueous solution of osmium chloride in a manner similar to that hereinbefore set forth. After activation of the osmium-impregnated titanited alumina, it may then be placed in an autoclave along with magnesium oxide. The catalyst system may then be used to hydrocrack sorbitol by treatment with hydrogen at a temperature of about 200° C. and a pressure of about 3000 psig, with desired lower polyols comprising glycerol, ethylene glycol, and 1,2-propanediol being recovered from the reaction mixture.

I claim as my invention:

1. A process for hydrocracking sorbitol which comprises treating said sorbitol at a temperature in the range of from about 150° C. to about 250° C. and a pressure in the range of from about 500 to about 5000 pounds per square inch gauge in the presence of hydrogen and a catalyst system consisting essentially of from about 1% to about 10% by weight of ruthenium composited on a titanited alumina support and a separate co-catalyst consisting essentially of from about 5% to about 50% by weight barium oxide to produce and then recover the resultant glycerol, ethylene glycol and 1, 2-propanediol.

* * * * *